(12) United States Patent
Campagna

(10) Patent No.: US 9,114,183 B2
(45) Date of Patent: Aug. 25, 2015

(54) PORTABLE ANTIMICROBIAL ULTRA VIOLET STERILIZER

(76) Inventor: Kenneth L. Campagna, Hilton, NY (US)

(*) Notice: Subject to any disclaimer, the term of this patent is extended or adjusted under 35 U.S.C. 154(b) by 36 days.

(21) Appl. No.: 13/606,180

(22) Filed: Sep. 7, 2012

(65) Prior Publication Data

US 2012/0328474 A1 Dec. 27, 2012

Related U.S. Application Data

(62) Division of application No. 12/761,859, filed on Apr. 16, 2010, now abandoned.

(60) Provisional application No. 61/171,346, filed on Apr. 21, 2009.

(51) Int. Cl.
| | | |
|---|---|---|
| *A61L 2/10* | (2006.01) | |
| *A61L 2/20* | (2006.01) | |
| *A61L 2/24* | (2006.01) | |

(52) U.S. Cl.
CPC . *A61L 2/10* (2013.01); *A61L 2/202* (2013.01); *A61L 2/24* (2013.01); *A61L 2202/14* (2013.01); *A61L 2202/16* (2013.01)

(58) Field of Classification Search
CPC ............. A61L 2/10; A61L 2/202; A61L 2/24; A61L 2202/14; A61L 2202/16
USPC ................................ 422/23, 24, 28
See application file for complete search history.

(56) References Cited

U.S. PATENT DOCUMENTS

| | | | |
|---|---|---|---|
| 5,664,340 A | 9/1997 | Brown | |
| 6,605,260 B1* | 8/2003 | Busted | 422/186.3 |
| 6,723,233 B1* | 4/2004 | Barnes | 210/167.11 |
| 6,877,248 B1 | 4/2005 | Cross | |
| 2003/0086818 A1* | 5/2003 | Holley et al. | 422/24 |
| 2004/0141875 A1 | 7/2004 | Doshi | |
| 2005/0226762 A1* | 10/2005 | Naarup | 422/4 |
| 2006/0076506 A1* | 4/2006 | Duthie, Jr. | 250/436 |
| 2007/0274879 A1 | 11/2007 | Millikin | |
| 2008/0206095 A1* | 8/2008 | Duthie | 422/24 |
| 2008/0260601 A1 | 10/2008 | Lyon | |
| 2010/0006804 A1 | 1/2010 | Sakovich | |
| 2011/0020175 A1* | 1/2011 | Collard et al. | 422/24 |

OTHER PUBLICATIONS

UVC/Ozone Cleaner, webpage, 1 page, http://www.jelight.com/uvo-ozone-cleaning.php, Apr. 21, 2009.
UV/Ozone ProCleaner™ and ProCleaner™ Plus, 1 page, webpage, http://www.bioforcenano.com/index.php?id=290, Apr. 21, 2009.
Bench top UV-Ozone Cleaning System, 1 page, webpage, http://www.samcointl.com/products/03_cleaner/02_uvozone/, Apr. 21, 2009.
UV Ozone tool disinfection cabinet (JB-208), 2 pages, webpage, http://www.alibaba.com/product-gs/677376541/UV_Ozone_tool_disinfection_cabinet_JB.html, Apr. 21, 2009.
CoolCLAVE™ Laboratory Bench to Sterilizer, 3 pages, webpage, http://www.genlantis.com/coolclave-sanitizer.html, Apr. 21, 2009.

* cited by examiner

*Primary Examiner* — Regina M Yoo
(74) *Attorney, Agent, or Firm* — Phillips Lytle LLP

(57) ABSTRACT

The present invention relates to a sterilization unit consisting of a cubical enclosure which uses a sequenced supply of ozone and ultraviolet radiation in the C band (UVC) wave length to sterilize. In use, an article to be sterilized is positioned atop a glass plate mounted between two sources of UVC radiation and ozone is first supplied to the enclosure for a period of 15 seconds to 60 minutes followed by a supply of UVC radiation for a period of 15 seconds to 60 minutes.

10 Claims, 4 Drawing Sheets

PORTABLE ANTIMICROBIAL ULTRA VIOLET STERILIZER

PRIORITY CLAIM AND RELATED APPLICATIONS

This divisional patent application claims the benefit of priority from provisional application U.S. Ser. No. 61/171,346 filed Apr. 21, 2009, U.S. Ser. No. 12/761,859 filed Apr. 16, 2010 and PCT/US10/031,527 filed Apr. 17, 2010. Said applications are incorporated by reference in their entirety.

BACKGROUND OF THE INVENTION

1. Field of the Invention

This invention relates generally to sterilizing systems, and more particularly, to a portable antimicrobial ultraviolet sterilizer for inactivating bacteria, viruses, fungi, prions, viroids and spores.

2. Description of Related Art

The use of portable sterilizing devices is known in the prior art. By way of illustration, medical facilities generally sterilize equipment by using autoclaves having a pressurized steam and superheated water process. This process is commonly used in microbiology, medicine, body piercing, veterinary science, dentistry, podiatry and metallurgy. Autoclaves are also used in curing carbon-fiber composite parts and rubber parts and for the treatment and sterilization of waste.

This steam sterilization process requires many steps and resources. A typical sterilization procedure using an autoclave requires distilled water, sterilization or biohazard bags, germicidal liquid spray wash, ultra sonic bathing and drying by air compressors.

Drawbacks of these autoclaves include high energy consumption, time waste due to multiple step disinfecting sequences, environmentally toxic and costly harsh germicidal chemicals, and the deteriorating effects of the steam process on stainless steel surfaces. There are also well known safety risks attendant with high power and high pressure machinery such as autoclaves, namely, where the water inside the autoclave has managed to become superheated, the pressure gauge may not indicate the presence of steam even though the temperature may be significantly higher than the local boiling point for water. If the autoclave is opened in this state and the superheated water is disturbed, a steam explosion becomes possible. This phenomenon can easily produce fatal burns to people in the vicinity of the explosion.

Other inherent limitations of this prior art technology exist because damp heat is used, and thus heat labile products (such as some plastics) cannot be sterilized this way or they will melt. Some paper or other products that may be damaged by the steam must also be sterilized another way.

The prior art sterilization systems such as steam autoclaving, even at increased temperatures, and ethylene oxide gas are not effective to prevent the transmission of prions and viroids via medical and surgical equipment. Current sterilization methods for heat-resistant instruments involves at least a four step process of immersion in hypochlorite followed by autoclaving, followed by a wash and rinse and then routine sterilization methods. Autoclaving generally involves immersion in a sodium hydroxide solution. This has well known drawbacks since hypochlorite and sodium hydroxide may be corrosive to some instruments, such as gold-plated instruments. There is also associated damage to the autoclaves caused by the sodium hydroxide. Autoclaving involves high pressure with steam to attain high temperatures. There is condensate formation during the cycle and hazardous substances such as sodium hydroxide condensate in the autoclave that causes corrosion. Some sterilizer manufacturers have stated that this will void their warranty. Additionally, autoclaving with sodium hydroxide poses hazards to operators as a result of the caustic vapors.

UV sterilization is known for use and sterilizing all manners of objects, and is used in purification and disinfection of water, air and surface. Throughout the years ultraviolet technology has become well established as a method of choice for its effectiveness, economy, safety, speed, ease of use, and because the process is free of by-products. UV sterilization is a rapid sterilization method, without the use of heat or chemicals. However, this process has not been reduced in practice to a readily accepted device and method for common usage.

UV sterilizers take many shapes and forms, and offer a variety of features. While these prior art UV sterilizers are presumably adequate for their intended purposes, none of these prior art devices are configured adequately to a portable device or applications that can be used as commercial medical grade sterilization units that replace conventional autoclaves or for low cost portable home units.

Therefore, there is a need for a new UV sterilization system platform to expand on the prior art, and in particular, a system that provides a portable unit that can be adapted to many applications and overcome the limitations of the prior art. This technology will have a dramatic impact upon public health in third world countries.

SUMMARY OF THE INVENTION

In accordance with the present invention, there is provided a portable sterilization unit consisting of an enclosure which uses an ultra violet radiation in the C band wave length to sterilize objects and surfaces by inactivating bacteria, viruses, fungi, prions, viroids and spores. The sterilization program sequentially irradiates articles with UV radiation at a wavelength that creates ozone (preferably 185 nm) followed by irradiation with germicidal UVC radiation wavelengths (preferably 253-255 nm). Although the invention is not so limited, an embodiment of the enclosure defining a cubical or generally airtight rectangular shaped chamber will be described in greater detail to illustrate the inventive concepts.

To facilitate access to the interior of the chamber for insertion of the objects to be sterilized, there is provided an entrance door on one or more faces of the cubical structure. There is also provided a shelf formed of silica or quartz glass or sapphire plate disposed substantially in the central portion of the enclosure's interior compartment. Mounted in the interior of the chamber is at least one ozone lamp that spans substantially the full length of the interior of the chamber. Preferably, at least an elongated UVC lamp spanning substantially the entire width of the chamber is used. More preferably, at least two elongated UVC lamps are used and disposed opposing one another such that one lamp is mounted on an upper portion of the chamber and a second lamp is mounted on a lower portion of the chamber below the glass plate shelf. Even more preferably, two elongated UVC lamps are mounted in an upper portion of the chamber and four elongated UVC lamps are mounted on a lower portion of the chamber below the glass plate shelf.

To sterilize, an object is placed on a silica or quartz glass or sapphire plate shelf in the interior of the chamber. The door is then closed. The ozone lamp is electrically powered and emits UV radiation in the interior of the chamber at 185 nm to create ozone gas in the chamber. Then, the UVC lamps are electrically powered and emit UVC radiation at 253.7 nm in the interior of the chamber. Any DNA based organisms on the objects being sterilized are destroyed and rendered harmless. It is further noted that using UVC type radiation in a self contained portable enclosure could be considered "green," environmentally safe, and controlled with no adverse effects or residuals.

Therefore, the purpose of the present invention is to present a UV sterilization system that has none of the disadvantages of prior art.

It is yet another object of the present invention to provide a UV sterilizer that minimizes or greatly reduces the power requirements of a sterilization system.

It is yet another object of the present invention to provide a UV sterilizer that minimizes or greatly reduces the multiplicity of steps and time requirements of the sterilization system.

It is yet another object of the present invention to provide a UV sterilizer that eliminates, minimizes or greatly reduces the resource requirements of the sterilization system.

It is yet another object of the present invention to provide a UV sterilizer that minimizes or greatly reduces the pressure requirements of the sterilization system.

It is yet another object of the present invention to provide a UV sterilizer that can be used with heat liable products and paper products.

It is yet another object of the present invention to provide a UV sterilizer that can be operated by a hand crank.

It is yet another object of this invention to provide a UV sterilizer that is economical from the viewpoint of the manufacturer and consumer, is susceptible of low manufacturing costs with regard to labor and materials, and which accordingly is then susceptible of low prices for the consuming public, thereby making it economically available to the buying public.

Whereas there may be many embodiments of the present invention, each embodiment may meet one or more of the foregoing recited objects in any combination. It is not intended that each embodiment will necessarily meet each objective.

Thus, having broadly outlined the more important features of the present invention in order that the detailed description thereof may be better understood, and that the present contribution to the art may be better appreciated, there are, of course, additional features of the present invention that will be described herein and will form a part of the subject matter of the claims appended to this specification. In this respect, before explaining at least one embodiment of the invention in detail, it is to be understood that the invention is not limited in its application to the details of construction and the arrangements of the components set forth in the following description or illustrated in the drawings.

The present invention is capable of other embodiments and of being practiced and carried out in various ways. Also it is to be understood that the phraseology and terminology employed herein are for the purpose of description and should not be regarded as limiting.

BRIEF DESCRIPTION OF THE DRAWINGS

The invention will be described by reference to the specification and the drawings, in which like numerals refer to like elements, and wherein.

Figure 1:
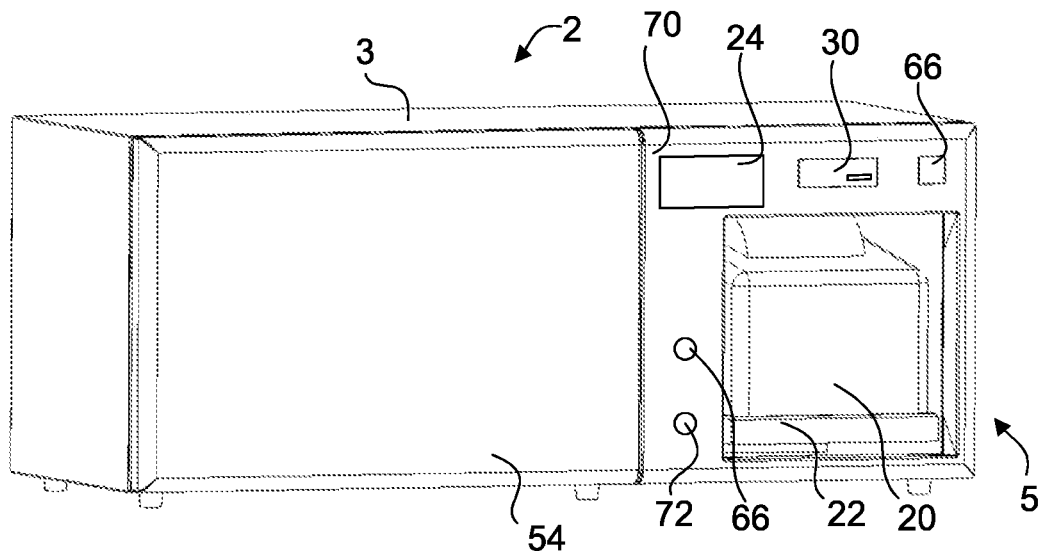
FIG. 1 is a top left front perspective view of a portable antimicrobial ultraviolet sterilizer according to the present invention.

The drawings are not to scale, in fact, some aspects have been emphasized for a better illustration and understanding of the written description.

PARTS LIST 2 sterilizer
3 sterilizer housing
4 ozone lamp
5 parts compartment
6 UVC lamp
8 chamber
10 ceiling of chamber
12 floor of chamber
14 side wall of chamber
16 glass shelf upon which an article being sterilized is placeable
18 stainless steel pin
20 printer
22 support slide assembly for printer
24 display
26 interior socket for receiving UVC wand
28 exterior socket for receiving UVC wand
30 user input/output interface
32 ozone lamp operation monitor
34 UVC lamp operation monitor
36 door state switch
38 door lock solenoid
40 controller
42 memory
44 clock
46 power selector
48 wall power
50 manual power generator
52 battery
54 entrance door
56 width of chamber
58 height of chamber
60 depth of chamber
62 curved corner
63 radius of curved corner
66 power switch
70 front wall of sterilizer
72 cancel switch
74 step of turning on ozone lamp
76 step of turning on UVC lamps
78 step of checking whether condition met to advance to step of turning on UVC lamps
80 step of checking whether condition met to advance to step of sterilization session complete
82 step of checking whether condition met to advance to step of sterilization session incomplete

DEFINITIONS OF TERMS USED IN THIS SPECIFICATION

The term Ultraviolet C is abbreviated as UVC and used throughout the document. UVC generally refers to radiation of wavelengths ranging from 280 nm to 100 nm and energy per photon ranging from 4.43 to 12.4 eV. Also, the term rectangular is understood to include the case where all sides of the geometric shape are of equal length, also known as an equilateral rectangle or a square.

DETAILED DESCRIPTION OF A PREFERRED EMBODIMENT

Figure 2:
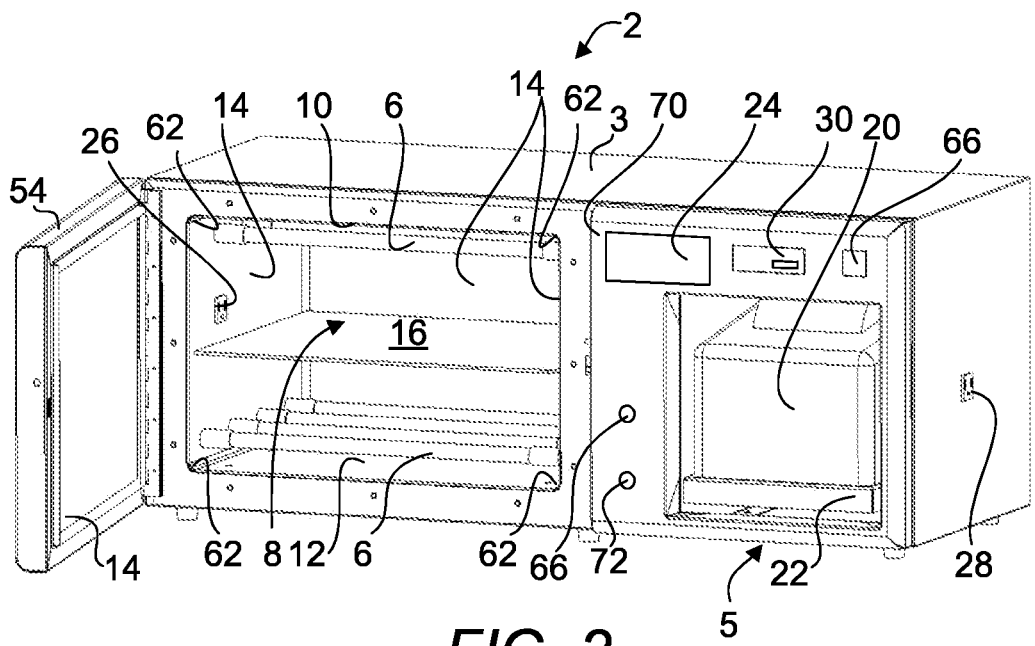
FIG. 2 is a top right front perspective view of the portable antimicrobial ultraviolet sterilizer of FIG. 1 with the entrance door open and showing the interior of a sterilizing chamber.

FIG. 1 is a top left front perspective view of a portable antimicrobial ultraviolet sterilizer. FIG. 2 is a top right front perspective view thereof with the entrance door open and showing the interior of a sterilizing chamber 8. Referring to FIGS. 1 and 2, a portable sterilizer 2 according to the present invention comprises a housing 3 which forms two compartments, a parts compartment 5 that houses electronic and electrical components and the chamber 8 that is used for the actual sterilization process. The parts compartment 5 houses operative and functional components of the unit such as a printer 20, ballasts, lamp holders, sockets, micro switches, blower motor, ballasts, cooling fan, power supply, wiring and circuit fuses.

The chamber 8 is a generally rectangular cavity having a ceiling 10, a floor 12 opposingly disposed to the ceiling 10 and four side walls 14 defining a spatial volume sufficient for irradiating an object by direct contact with UVC wavelengths. The chamber 8 is preferably rectangular and is formed of plastic, metal, stainless steel or other material that is opaque to UV radiation and conducive to reflecting or scattering UV radiation within the chamber 8.

While the chamber 8 may also be made spherical, a rectangular chamber is more easily manufactured using conventional manufacturing techniques than a spherical chamber. When a rectangular chamber is used, the applicant discovered that it is advantageous to provide curved corners in order to enhance scattering of ultravioulent radiation within the chamber 8.

In a preferred embodiment, the chamber walls are formed of 304-308 grade stainless steel. The chamber's interior surfaces are preferably highly polished mirror finish stainless steel to reflect and scatter the UVC radiation within the chamber 8. In another embodiment, the interior surface is coated with highly reflective white paint coating.

The size of the chamber 8 may vary depending upon the application, however, in most embodiments, the size will be such that the unit is portable. In the embodiment depicted in FIG. 1, the sterilizer approximates the size of a conventional microwave oven. Typical embodiments comprise a chamber volume ranging from about 1500 cubic inches to about 2500 cubic inches, preferably from about 1700 cubic inches to about 1900 cubic inches.

To facilitate access to the interior of the chamber 8 for insertion of the objects to be sterilized, there is provided an entrance door 54 on one or more walls of the chamber 8. In one embodiment, the entrance door 54 is hingeably connected to an edge of the chamber 8 and secured using a magnetic latch on an opposing edge. In another embodiment, the entrance door 54 is secured using a mechanical latch, solenoid or electric magnetic coil. For ease of description, this side wall 14 provided by the entrance door 54 will be referenced as the front, however, it is to be understood that any side may contain an entrance door or even several walls of the chamber 8 may feature an entrance door 54. The entrance door 54 preferably contains a door gasket (not depicted) to create and maintain a seal when the door is in the closed position. In one embodiment, a handle is affixed to the entrance door 54 to facilitate easy opening of the door 54 by a user. As will be appreciated, any size or configuration of handle may be used.

On the exterior of the chamber 8, preferably on the sterilizer front wall 70, is disposed such display and user input/output interface as may be desired for operation of the sterilizer. In the embodiment depicted in FIG. 1, there is provided a visual display 24 and a user input/output interface 30. In one embodiment, the user input/output interface 30 comprises a key pad or touch pad for receiving and transmitting user input to the controller 40 and a communicating means to a device operably connected to the user input/output interface 30. In an embodiment not shown, the communicating means comprises a wireless terminal capable of transmitting data wirelessly from the controller to a device operably connected to the controller or from the device to the controller. The display is configurable to display any number of indicators relating to the operation of the sterilizer.

In one embodiment, a value is displayed to indicate the usage hours of each UVC and ozone lamp in the sterilizer, a value is displayed to indicate the progress of a sterilization session and a value is displayed to indicate whether a sterilization session has been completed. All such indications aid a user in knowing when to change a UVC and/or ozone lamp and perform other periodic maintenance or testing activities and whether a sterilization session was complete and/or successful in sterilizing the articles. In another embodiment not shown, an analog or digital timer dial is provided and is operably connected to the controller. As the timer dial is turned, a sterilization session is started. As the timer dial stops, the active sterilization session is terminated. When a timer dial is provided, the timer dial is preferably one that allows for 0-60 minutes to indicate the duration of a sterilization session. It is to be appreciated that other equivalent user interfaces may be used to set a sterilization timer. The user input/out interface and visual display may also be located on other portions of the sterilizer.

There are also provided a power (on-off) switch 66 and an operation indicator 68 (for example a light) to indicate when the unit is in operation. Alternatively, an operator indicator is digitally displayed on the display 24 in lieu of using a separate operation indicator. In the on state, the power switch 66 connects the controller and all components operably connected to it and all lamps to a power source. In the off state, the power switch 66 removes the controller and all components operably connected to it and all lamps from the power source.

Referring to FIG. 2, an exterior socket 28 allows a UVC wand to be operably connected to the sterilizer for external use. A UVC wand may be connected to a wall socket directly. However, a UVC wand that is connected to the sterilizer receives the benefit of operating using a program set in the sterilizer. This is especially useful for surfaces which cannot be contained within the chamber 8, such as, for example, shelves, chairs, tables, equipment and the like. When used with the exterior socket, the UVC wand allows surfaces to be treated by waving the wand over the surface. The wand is preferably coupled with a half moon safety shield to protect the user from UVC radiation during use.

An interior socket 26 allows a UVC wand to be operably connected to the interior of the chamber 8 for supplemental UVC radiation. A UVC wand is most beneficially used on an object to be sterilized if the object is generally elongated and has a narrow lumen which the radiation of the UVC lamps 6 may not sufficiently reach. Placing the wand in the lumen provides direct UVC radiation to these surfaces to maximize the sterilization effects.

Figure 3:
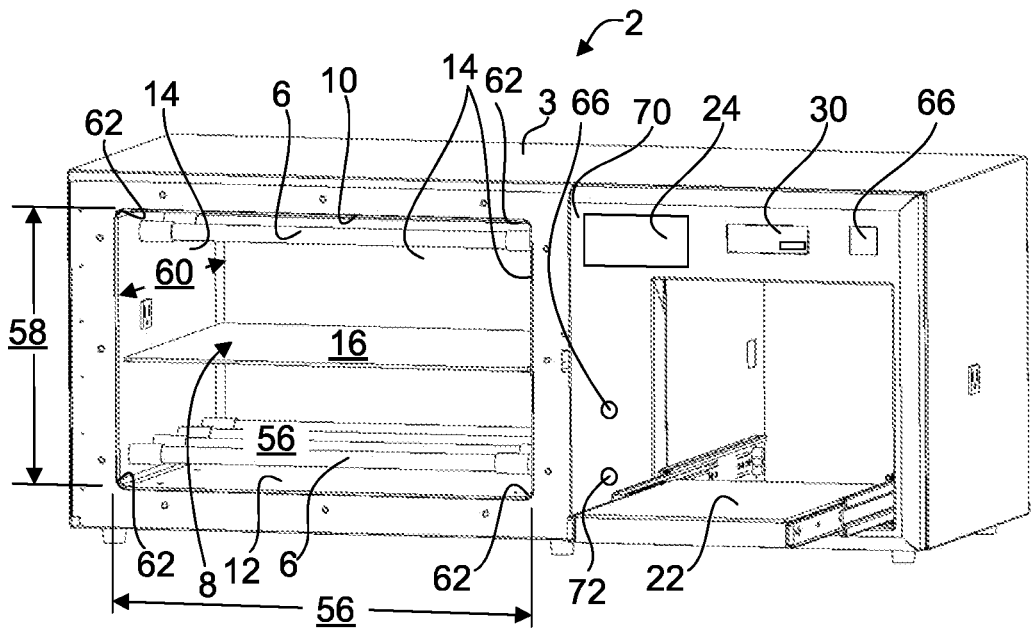
FIG. 3 is a top right front perspective view of the portable antimicrobial ultraviolet sterilizer of FIG. 1 with the entrance door removed to further illustrate dimensions of the sterilizing chamber and the printer of FIG. 1 removed to further illustrate the support slide assembly used to hold the printer.
Figure 4:
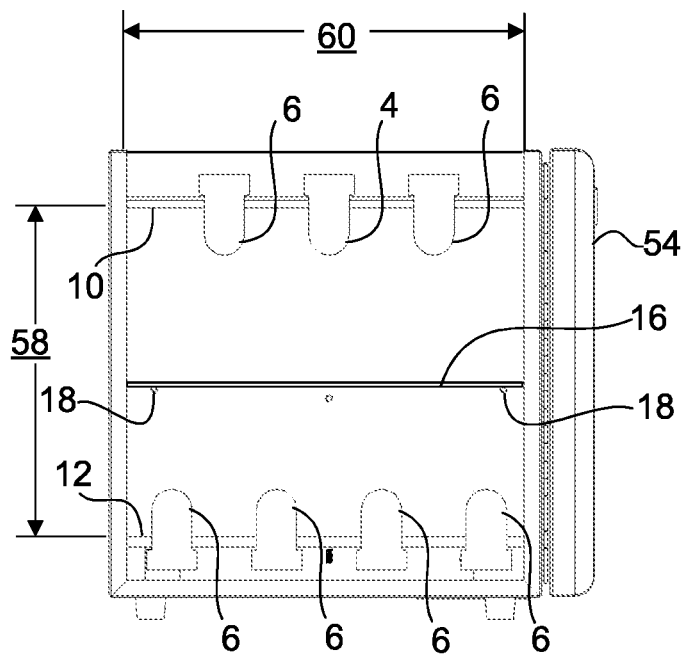
FIG. 4 is a partially transparent left side orthogonal view of the portable antimicrobial ultraviolet sterilizer of FIG. 1 illustrating the spatial relationships of UVC lamps, an ozone lamp and a glass shelf of the present invention.

FIG. 3 is a top right front perspective view of the portable antimicrobial ultraviolet sterilizer of FIG. 1 with the entrance door 54 removed to further illustrate dimensions of the sterilizing chamber and the printer of FIG. 1 removed to further illustrate the support slide assembly used to hold the printer 20 of FIG. 2. FIG. 4 is a partially transparent left side orthogonal view of the portable antimicrobial ultraviolet sterilizer of FIG. 1 illustrating the spatial relationships of UVC lamps 6, an ozone lamp 4 and a glass shelf 16 of the present invention. Mounted in the interior of the chamber 8 is at least one UVC lamp 6 that spans substantially the full width 56 of the chamber 8. Preferably, as depicted in FIG. 4, six functionally equivalent and elongated UVC lamps 6 are used. Two are substantially aligned with the width 56 of the chamber and disposed substantially symmetrically about the depth 60 and width 56 of the ceiling 10 and provide combined working UV power output of at least 8 watts. Four are substantially aligned with the width 56 of the chamber and disposed substantially symmetrically about the depth 60 and width 56 of the floor 12 and provide combined working UV power output of at least 16 watts. Other lamp shapes (such as U-shaped) and mounting locations may be used as long as radiation is directed such that all portions of the chamber 8 receive UVC radiation. In one embodiment, the width 56, depth 60 and height 58 are preferably about 15 inches, 12 inches and 12 inches, respectively. However, other suitable dimensions can be used provided that the output requirements defined elsewhere herein of the ozone and UVC lamps are met.

The low pressure UVC lamps are most effective, because they emit most of the radiant energy in the germicidal wavelength of 253.7 nm to 254.3 nm in the UVC and germicidal part of the spectrum. The ozone lamp, preferably a high or very high ozone lamp, emits a radiation below 200 nm, and preferably at 185 nm, which wavelengths produce ozone. Ozone has deodorizing properties and is in itself a bactericidal and fungicidal agent. This gaseous ozone contacts surfaces of the equipment that are difficult or impossible to contact with the UVC waves, getting into hollow portions, small cavities, crevices and other apertures where microbes, fungi, yeast, viruses and other germs may be hosted.

Preferably, as depicted in FIG. 4, an elongated ozone lamp 4 is disposed substantially centrally on the ceiling and parallel to and substantially spanning the width 56 of the chamber 8. Other ozone lamp shapes and mounting locations may also be used provided that the object to be sterilized is fully exposed to ozone generated by such an ozone lamp.

There is also provided a shelf 16 formed of silica or quartz glass or sapphire plate disposed substantially centrally in the chamber 8 and/or between the two groups of UVC lamps on the ceiling 10 and on the floor 12 with the shelf's 16 plane substantially parallel to the ceiling 10 or floor 12. Referring to FIG. 4, the shelf 16 is supported by one or more stainless steel pins 18 or other mounting means known in the art. The silica or quartz glass or sapphire plate is of a grade that allows at least 50% transmission of UVC short wave radiations, preferably at least 55% transmission. A silica or quartz glass or sapphire plate must be used because ordinary window glass passes about 90% of the light above 350 nm, but blocks over 90% of the light below 300 nm, the wavelength of the UVC lamp radiation. Though unintendedly, the glass plate effectively divides the chamber 8 into two portions, i.e., an upper portion and a lower portion. In use, an object to be sterilized is disposed on the upper portion. Preferably, an ozone lamp 4 is beneficially disposed on the upper portion of the chamber 8, enabling ozone generated by the ozone lamp 4 to penetrate openings of the object to be sterilized.

Figure 5:
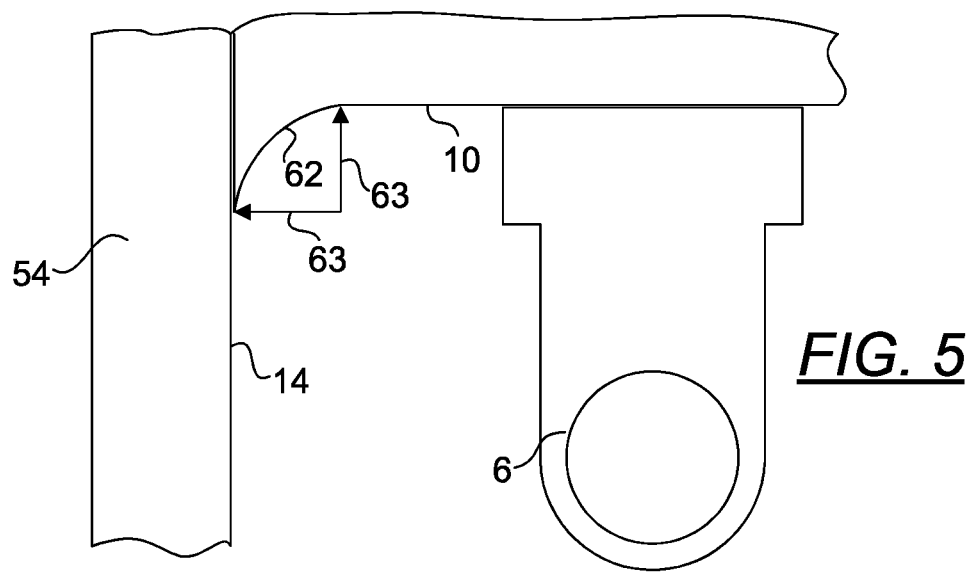
FIG. 5 is a partial orthogonal view of a curved corner of FIG. 1 illustrating the use of a curved corner between a chamber's entrance door and its adjacent walls.

FIG. 5 is a partial orthogonal view of a curved corner of the chamber 8 of FIG. 2, illustrating the use of a curved corner between the entrance door 54 and one of its adjacent walls, for example, the ceiling 10. Curved corners promote reflection and scattering of UVC radiation and reduce the number of UVC lamps required to provide sufficient UVC radiation coverage within the chamber 8. Curved corners also reduce the number of surfaces (walls) on which UVC lamps are required, thereby simplifying the design of the sterilizer and reducing associated manufacturing and maintenance costs. As depicted, a curved corner 62 is formed on the ceiling 10 of the chamber 8 such that when the entrance door 54 is closed, a side wall 14 is formed, continuing the profile formed by the curved corner 62 of the ceiling 10 onto a vertical side wall 14. The radius of the curved corner is defined by the relationship where the ratio of the radius to the width 56 of the chamber 8, height 58 of the chamber 8 or depth 60 of the chamber 8 preferably ranges from 0.0026 to 0.1. In one preferred embodiment, the radius is about 0.25 inches.

The UVC lamps 6 use an ultra violet radiation in the shortwave ultraviolet radiation, in the "C" band (100 to 280 nanometers) to sterilize objects and surfaces by inactivating bacteria, viruses, fungi, prions, viroids and spores. At wavelengths below 254 nm, UV-C (UVC) is also referred to as UVGI (ultraviolet germicidal irradiation). Ultraviolet Germicidal Irradiation (UVGI) is a term used by Federal Agencies such OSHA, NIOSH and the CDC when referring to UVC at 253.7-254.3 nm. UVC penetrates the outer structure of the cell and alters the DNA molecule, preventing replication and causing cell death. Specifically, UVC light at 253-254 nm causes damage to the nucleic acid of microorganisms by forming covalent bonds between certain adjacent bases in the DNA. The formation of such bonds prevents the DNA from being unzipped for replication, and the organism is unable to reproduce. In fact, when the organism tries to replicate, it dies.

The present invention is effective in killing prions, in particular prion glycoproteins. Thus, the present device and method provide an effective microbiocidal treatment against transmittable prion diseases that occur in humans and animals. As an illustrative example, the present invention kills the prions associated with the transmissible spongiform encephalopathy (TSE) known more commonly as Creutzfeldt-Jakob disease (CJD), bovine spongiform encephalopathy (mad cow disease) in cattle, and scrapie in sheep. These prions are also suspected to cause Alzheimer's disease and other brain plaque conditions. As another illustrative example, the present invention also kills the viroids associated with Hepatitis D.

The combination of ozone and UVC radiation treatment at the dosage mentioned elsewhere in the specification is capable of inactivating microorganisms such as prion, viroids, SARS, AIDS, HIV, e-coli, *Agrobacterium lumefaciens* 5, *Pseudomonas aeruginosa* (Environ.Strain) 1,2,3,4,5, 9, *Bacillus anthracis* 1,4,5,7,9 (anthrax veg.), *Pseudomonas aeruginosa* (Lab. Strain) 5,7, *Bacillus anthracis* Spores (anthrax spores), *Pseudomonas fluorescens* 4,9, *Bacillus megatherium* Sp. (veg) 4,5,9, *Rhodospirillum rubrum* 5, *Bacillus megatherium* Sp. (spores) 4,9, *Salmonella enteritidis* 3,4,5,9, *Bacillus paratyphosus* 4,9 *Salmonella paratyphi* (Enteric Fever) 5,7, *Bacillus subtilis* 3,4,5,6,9, *Salmonella* Species 4,7,9, *Bacillus subtilis* Spores 2,3,4,6,9, *Salmonella typhimurium* 4,5,9 *Clostridium tetani, Salmonella typhi* (Typhoid Fever) 7, *Clostridium botulinum Salmonella, Corynebacterium diphtheriae* 1,4,5,7,8,9, *Sarcina lutea* 1,4,5,6,9, Dysentery bacilli 3,4,7,9, *Serratia marcescens* 1,4,6,9, *Eberthella typhosa* 1,4,9, *Shigella dysenteriae*—Dysentery 1,5,7,9, *Escherichia coli* 1,2,3,4,9, *Shigella flexneri*—Dysentery 5,7, *Legionella bozemanii* 5, *Shigella paradysenteriae* 4,9 *Legionella dumoffill* 5, *Shigella sonnei* 5, *Legionella gormanil* 5, *Spirillum* rubrum 1,4,6,9, *Legionella micdadei* 5, *Staphylococcus albus* 1,6,9, *Legionella longbeachae* 5, *Staphylococcus aureus* 3,4,6,9, *Legionella pneumophila* (Legionnaire's Disease), *Staphylococcus epidermidis* 5,7, *Leptospira canicola*-Infectious Jaundice 1,9, *Streptococcus faecaila* 5,7,8, *Leptospira interrogans* 1,5,9, *Streptococcus hemolyticus* 1,3,4,5,6,9, *Micrococcus candidus* 4,9, *Streptococcus lactis* 1,3,4,5,6, *Micrococcus sphaeroides* 1,4,6,9, *Streptococcus pyrogenes, Mycobacterium tuberculosis* 1,3,4, 5,7,8,9, *Streptococcus salivarius, Neisseria catarrhalis* 1,4, 5,9, *Streptococcus viridans* 3,4,5,9, *Phytomonas tumefaciens* 1,4,9, *Vibrio comma* (Cholera) 3,7, *Proteus vulgaris* 1,4,5,9, *Vibrio cholerae* 1,5,8,9, *Aspergillus amstelodami, Oospora lactis* 1,3,4,6,9, *Penicillium chrysogenum, Aspergillus flavus* 1,4,5,6,9, *Aspergillus glaucus* 4,5,6,9, *Penicillium digitatum* 4,5,6,9, *Aspergillus niger* (breed mold) 2,3,4,5,6,9, *Penicillium expansum* 1,4,5,6,9, *Mucor mucedo, Penicillium roqueforti* 1,2,3,4,5,6, *Mucor racemosus* (A & B) 1,3,4,6,9, *Rhizopus nigricans* (cheese mold) 3,4,5,6,9, *Chlorella vulgaris* (algae) 1,2,3,4,5,9, *Giardia lamblia* (cysts) 3, Blue-green Algae, Nematode Eggs 6, *E. hystolytica, Paramecium* 1,2,3, 4,5,6,9, Adeno Virus Type III 3, Influenza 1,2,3,4,5,7,9, Bacteriophage 1,3,4,5,6,9, Rotavirus 5, Coxsackie, Tobacco Mosaic 2,4,5,6,9, Infectious Hepatitis 1,5,7,9, Baker's Yeast 1,3,4,5,6,7,9, *Saccharomyces cerevisiae* 4,6,9, Brewer's Yeast 1,2,3,4,5,6,9, *Saccharomyces ellipsoideus* 4,5,6,9, Common Yeast Cake 1,4,5,6,9, *Saccharomyces* sp. 2,3,4,5,6, 9.

Figure 6:
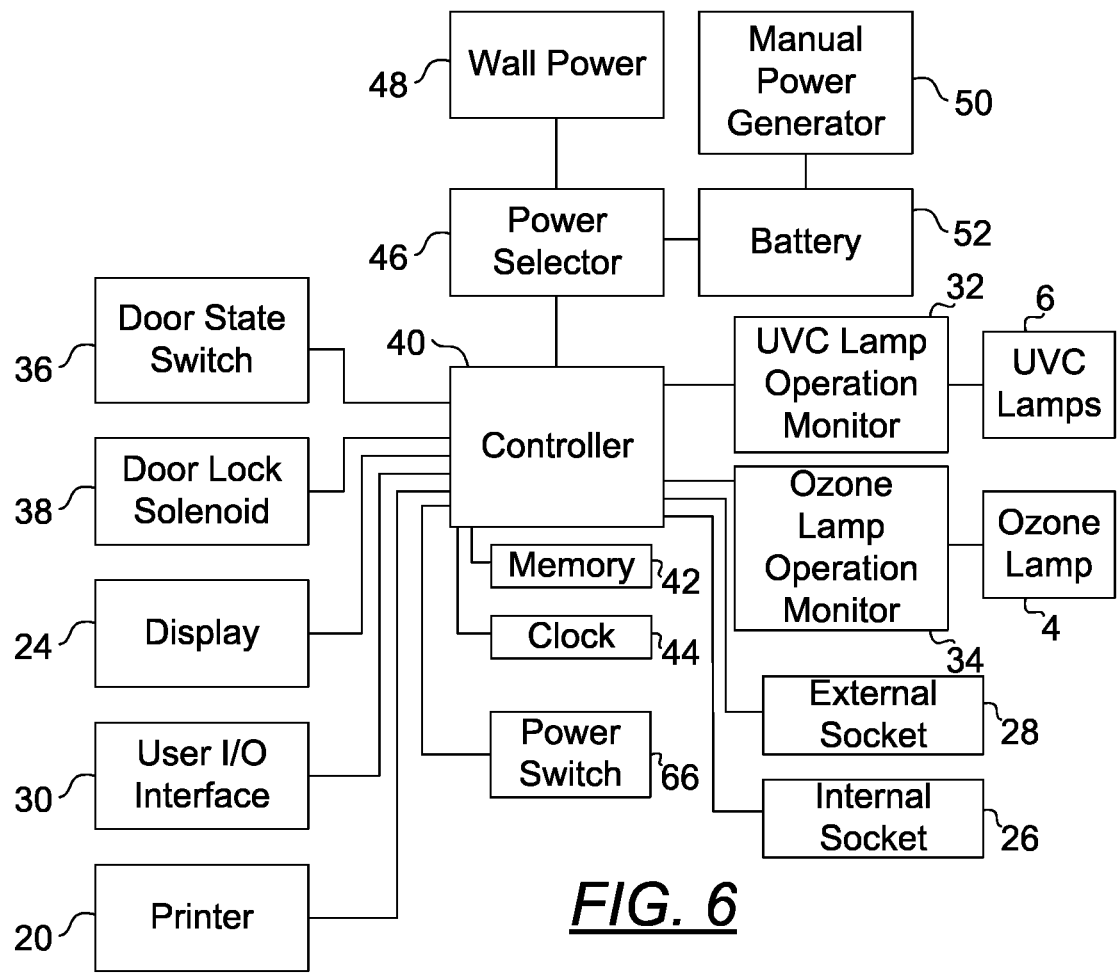
FIG. 6 is a block diagram of one preferred embodiment of the present invention.

FIG. 6 is a block diagram of one preferred embodiment of the present invention. A controller 40 is provided to control operations of the sterilizer 2. A user Input/Output interface 30 functionally connected to the controller 40 is further provided to receive inputs from a user or a device and send outputs to the user or the device. By way of example and not limitation, the device is a keypad, touch pad, computer, a monitor, an MP3 player, MP4 player, a digital display, an ipod, an ipad, a finger print reader, a security card reader, an entry code reader, a smart phone and the like. A display 24 functionally connected to the controller 40 is provided to display the result of a sterilization session or communicate other pertinent information from the controller to a walk-up user. A printer 20 functionally connected to the controller 40 is provided to receive and provide a printout of the result corresponding to a sterilization session if requested. A power switch 66 is provided to enable or halt all operations of the sterilizer 2. A door state switch 36 functionally connected to the controller is provided to indicate whether the entrance door 54 is open. In the off state, the power switch 66 removes power from all components of the sterilizer, thereby halting all activities including programming of the sterilizer. When the door state switch 36 indicates an opened entrance door 54, the user may still program the controller in order to set a sterilizing program.

There are provided six UVC lamps 6 and an ozone lamp 4 that are operably connected to the controller 40. A UVC lamp operation monitor 32 functionally connected to the controller 40 is further provided to detect proper operation of the UVC lamps 32 and it provides an indication to the controller 40 whether the UVC lamps are functioning properly. An example parameter monitored by the lamp operation detector 32 is the amount of electrical current at an electrical potential the UVC lamps 6 source to function at the level expected to provide proper sterilization. If the electrical current at the electrical potential received by the UVC lamps 6 deviates from a predetermined range, a fault condition is issued by the UVC lamp operation monitor 32 and received by the controller 40. Similarly, an ozone lamp operation monitor 34 functionally connected to the controller 40 is further provided to detect the proper operation of the ozone lamp 4. If the electrical current at an electrical potential received by the ozone lamp 4 deviates from a predetermined range, a fault condition is issued by the ozone lamp operation monitor 34 and received by the controller 40. In one embodiment, the controller 40 further communicates the fault condition to a remote server which then specifies the failure and a need for service.

The controller 40 further comprises a memory 42 and a clock 44. The result of a sterilization session may be saved in the memory 42 for later retrieval. A section of the memory 42 is preferably reserved for long-term storage of sterilization session data and is erasable only by a trained professional. This long-term storage facilitates auditing of sterilization session data which can be traced back for a number of years. In another embodiment, sterilization session data is additionally transmitted to an offsite location for storage or notification purposes. The clock 44 enables the controller to perform time-keeping operations such as providing realtime time stamps to a sterilization session. A typical sterilization session result comprises an indication whether a sterilization session runs to completion. A successfully completed sterilization session is defined as a sterilization session in which a fault has not occurred during the entire duration of the sterilization session. A successfully completed sterilization session however does not necessarily indicate a successful sterilization session. In the present embodiment, for each sterilization session, an unused UVC test strip is further provided and substantially centrally disposed prior to the commencement of each sterilization session such that the proper functioning of the UVC lamps can be verified. At the end of the sterilization session, the evidence of exposure to the UVC lamps on the UVC test strip is visually read, quantified and compared to a pre-established standard for sufficient UVC exposure corresponding to a pass condition. Similarly, in the present embodiment, an unused ozone test strip is further provided and disposed on the upper surface of the glass plate 16 prior to the commencement of each sterilization session such that the proper functioning of the ozone lamp can be verified. At the end of a sterilization session, the evidence of exposure to the ozone lamp on the ozone test strip is visually read, quantified and compared to a pre-established standard for sufficient ozone exposure corresponding to a pass condition. A pass condition from both UVC and ozone test strips and the successful completion of a sterilization session constitute a successful sterilization session. If a sterilization report is desired, the visually determined test strips data is entered manually via the user Input/Output interface 30 such that the controller 40 can determine whether the sterilization session was successful and saves such a result to the memory 42.

Alternatively, an automatic indication of a successful sterilization session may also be provided by using a UVC detector and an ozone detector, both functionally connected to the controller 40. At the end of a sterilization session, the evidence and level of exposure to the ozone lamp and UVC lamp on the ozone and UVC test strips are automatically read respectively, quantified and compared to a their corresponding pre-established standards for sufficient ozone and UVC exposure respectively corresponding to a pass condition.

There is further provided a lock solenoid 38 functionally connected to the controller 40 for locking the entrance door 54 in its closed position. For safety reasons, before a sterilization session can begin, the controller 40 checks whether the entrance door 54 is closed by receiving a reading from the door state switch 36. If the entrance door 54 is determined to be closed, the lock solenoid 38 is then activated such that the entrance door 54 is locked. Upon the completion or cancellation of a sterilization session, the ozone and UVC lamps are deactivated and the lock solenoid 38 is deactivated such that the entrance door 54 becomes unlocked.

An internal socket 26 functionally connected to the controller 40 is further provided in the interior of the chamber 8. The sterilization program set for the UVC lamps 8 is applied to a UVC wand connected to the internal socket 26. By way of illustration, U.S. Pat. Pub. No. 20080260601 discloses a UV sterilizing wand which can be adapted to be powered by plugging its power cord into the internal socket 26, which patent application is incorporated by reference in its entirety herein. Such an additional sterilizing source is most beneficial when an object to be sterilized has a generally opaque structure consisting of narrow openings which cannot be easily reachable by using merely the UVC lamps 6 of the sterilizer 2 according to the present invention.

An external socket 26 functionally connected to the controller 40 is further provided on the exterior of the chamber 8. The sterilization program set for the UVC lamps 8 is applied to a UVC wand connected to the external socket 28. Alternatively, a separate sterilization program can be applied. Generally, a wand is used externally when an object to be sterilized is too big to be placed within the chamber 8.

The sterilizer 2 typically receives power from a conventional AC power source such as a wall power outlet 48. However, in certain circumstances where wall power is limited, unavailable or not easily accessible, a battery 52 can be functionally connected to the controller 40 as an alternative power source. A power selector 46 is used to selectably allow the user to select the power source from which to power the sterilizer 2. The power selector 46 is essentially a manual single pole double throw switch which selectively connects the wall power 48 or battery 52 to the controller 40. An inverter is provided to convert the battery DC power to AC power in order to power the controller 40. It shall be appreciated that other equivalent means of switching power source may be suitably employed. It shall also be appreciated that the controller 40 may or may not provide power directly to any components that require electrical power to run. Conventionally, power electronics receive their power directly from the power source and not through a controller. In a preferred embodiment, a manual power generator 50 is further provided to allow a user to recharge the battery 52. A manual power generator 50 is essentially a device that converts human power to electrical power. Though not required, it is generally a hand crank in the form of a rotary device is fitted with a handle which can be turned to create DC power. In this instance, the battery 52 is a rechargeable battery. It should be appreciated that various other means of generating power to be stored in the battery 52 are readily available to those skilled in the art. For instance, electrical energy may alternatively be generated from solar panels and wind turbines.

Figure 7:
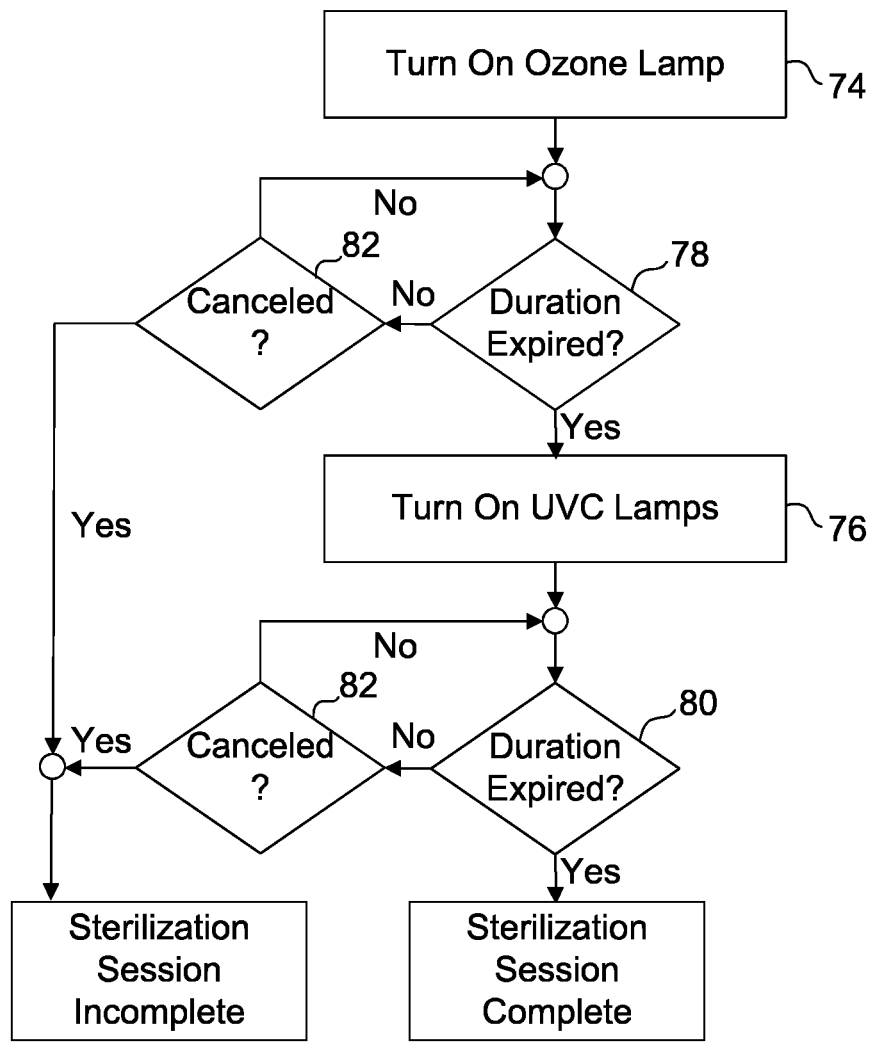
FIG. 7 is a flow chart depicting a present novel method used in a sterilization session to destroy or render harmless any DNA based organisms on objects being sterilized.

FIG. 7 is a flow chart depicting a present novel method used in a sterilization session to destroy or render harmless any DNA based organisms on objects being sterilized. To sterilize, an object is placed on the glass shelf 16 in the interior of the chamber 8 as depicted in FIG. 2. The entrance door 54 is then closed. The method comprises step of turning on 74 ozone lamp for a first predetermined duration of from 15 seconds to 60 minutes, preferably from 15 to 60 seconds. A timer corresponding to the predetermined duration is started. At least one ozone lamp 4 capable of producing from at least 0.25 to 10 grams per hour of ozone is used. In one embodiment, an ozone lamp 4 capable of emitting UV radiation at wavelength of about 185 nm is used. Referring to FIGS. 6 and 7, the controller 40 checks whether the timer has expired 78. If the timer has expired, the controller 40 continues to execute the preprogrammed next step. The controller 40 further checks whether an event has occurred that canceled the current sterilization session 82. For instance, if the ozone lamp operation monitor 34 detects a fault condition, the sterilization session will be stopped, rendering the sterilization session incomplete.

The method further comprises step of turning on 76 at least one UVC lamp but preferably six UVC lamps for a second predetermined duration of from 15 seconds to 60 minutes, preferably from 15 to 60 seconds. A timer corresponding to the predetermined duration is started. In a preferred embodiment, at least one UVC lamp capable of supplying UVC radiation at a wavelength of about 253.7 nm and dosage of from at least 100 to 800 microwatts per square centimeter at one meter from the UVC lamp is used. Referring to FIGS. 6 and 7, the controller 40 checks whether the timer has expired 80. If the timer has expired, the controller continues to indicate that the sterilization session has been completed. If the timer continues to run, the controller 40 further checks whether an event has occurred that canceled the current sterilization session 82. For instance, if the ozone lamp operation monitor 34 detects a fault condition, the sterilization session will be stopped, rendering the sterilization session incomplete.

The ozone molecules formed as a result of the ozone lamp absorb ultraviolet radiation having wavelengths between 240 and 310 nm. Upon absorbing ultraviolet radiation of wavelength of 254 nm, each triatomic ozone molecule becomes diatomic molecular oxygen molecule $O_2$ plus a free oxygen atom O, thereby reducing the ozone $O_3$ concentration to an acceptable level as depicted in the following chemical reaction.

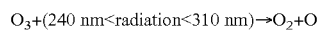

$$O_3 + (240\ nm < radiation < 310\ nm) \rightarrow O_2 + O$$

As it should be appreciated by those skilled in the art, ozone is an oxidative agent which must be avoided when concentration rises above 0.05 ppm in an indoor environment. Conventionally, ozone evacuation or treatment becomes necessary when ozone concentration rises beyond a level capable of producing health hazards. Such evacuation or treatment requires purpose-built equipment which adds to the cost of producing such a sterilizer. Applicant discovered that by sequencing the operation of the ozone and UVC lamps, production and neutralization of ozone is accomplished within a sterilization session without requiring additional steps or equipment. The ozone generated and used in the sterilization session is completely decomposed to form oxygen molecules and oxygen atoms, thereby rendering the sterilizer safe to be handled without additional treatment. At the successful conclusion of a sterilization session, any DNA based organisms on the objects being sterilized are destroyed and rendered harmless.

In one aspect, the equipment to be sterilized is first rinsed or immersed in an antimicrobial or biocidal solution. Preferably, the solution is a non-alcohol based cleaning solution. In one aspect, the equipment is immersed in a solution prepared according to the teachings in United States Published Patent Application 20100006804 to Sakovich et al for "A highly protonated, supercharged, low pH, non-corrosive composition," which patent application is incorporated by reference in its entirety herein. This product is sold under the trade name Saniphex by Odysseus Industries, Inc., 8348 Little Road, New Port Richey, Fla.

What has been disclosed, is a portable antimicrobial ultraviolet sterilizer for inactivating bacteria, viruses, fungi, prions, viroids and spores. Obviously, many modifications and variations of the invention are possible in light of the above teachings. It is therefore understood that the invention is not to be limited by the single embodiment shown in the drawings and described in the description, which are given by way of example and not of limitation, but only in accordance with the scope of the appended claims. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent construction insofar as they do not depart from the spirit and scope of the conception regarded as the present invention.

What is claimed is:

1. A method of medical grade sterilization comprising:
   (a) providing a housing with an airtight chamber possessing a volume no larger than 2500 inch$^3$, wherein the airtight chamber has one or more compartments;
   (b) providing one or more components configured to emit UVC radiation or generate ozone or both, wherein the UVC radiation and the ozone are confined within the one or more compartments of the airtight chamber;
   (c) providing an article for sterilization, wherein the article is capable of fitting within the airtight chamber;
   (d) exposing the article first to the ozone for at least 15 seconds at about 0.25 g/hr to about 10 g/hr; and
   (e) exposing the article to the UVC radiation for at least 15 seconds after the ozone exposure, wherein the UVC radiation exposure is at about 100 µW/cm$^2$ to about 800 µW/cm$^2$, and wherein the ozone concentration is no greater than 0.05 ppm within the airtight chamber following the UVC exposure, and further wherein the medical grade sterilization occurs in the absence of ozone heating.

2. The method of claim 1, wherein the UVC radiation is emitted at a λ of about 254 nm and the ozone is emitted at a λ of about 185 to 200 nm.

3. The method of claim 1, wherein the one or more compartments are separated by a shelf composed of silica, quartz, glass or sapphire, and wherein the shelf transmits at least 55% of the UVC radiation.

4. The method of claim 1, wherein one or more interior corners of the airtight chamber are curved, and wherein the curvature possesses a radius to width, height, or depth of the airtight chamber of about 0.0026 to 0.1.

5. The method of claim 1, wherein the one or more components do not emit UVA or UVB radiation.

6. The method of claim 1, wherein the one or more components are positioned at an inner-top and an inner-bottom surface of the airtight chamber as ozone lamps or UVC lamps or both.

7. The method of claim 1, wherein the exposing of step (d) or step (e) or both occurs for less than 1 minute.

8. The method of claim 1, wherein the medical grade sterilization occurs in the absence of one or more parameters selected from the group consisting of water, steam, liquid spray washing, condensation, drying, superheated gas, damp heat, pressures greater than about 1 atm, temperatures greater than 50° C., metal corrosion, chemical sterilization and caustic vapors.

9. The method of claim 1 further comprising: providing UVC or ozone test strips or both.

10. The method of claim 1 further comprising: washing the article with an antimicrobial solution prior to the exposing of step (d).

\* \* \* \* \*